United States Patent

Lochmann et al.

[11] 3,971,816
[45] July 27, 1976

[54] ESTERS OF CARBOXYLIC ACIDS FORMALLY SUBSTITUTED BY SODIUM OR POTASSIUM IN TE ALPHA-POSITION AND THE METHOD FOR THEIR PREPARATION

[75] Inventors: Lubomir Lochmann; Jiri Trekoval, both of Prague, Czechoslovakia

[73] Assignee: Ceskoslovenska akademie ved, Prague, Czechoslovakia

[22] Filed: Nov. 21, 1974

[21] Appl. No.: 525,855

[30] Foreign Application Priority Data
Nov. 26, 1973  Czechoslovakia.................. 8135-73
Sept. 4, 1974  Czechoslovakia.................. 6085-74

[52] U.S. Cl. .................. 260/410.9 R; 260/476 R; 260/478
[51] Int. Cl.² ........................................... C11C 3/02
[58] Field of Search .............. 260/410.9 R, 476 R, 260/478

[56] References Cited
UNITED STATES PATENTS

| | | | |
|---|---|---|---|
| 2,909,565 | 10/1959 | Pree | 260/413 |
| 3,123,628 | 3/1964 | Clossen | 260/486 R |
| 3,674,836 | 7/1972 | Creger | 260/410.9 R |

OTHER PUBLICATIONS
J. Am. Chem. Soc., 1970, 92, 3222.
J. Organomet. Chem., 1964, 1, 476.

*Primary Examiner*—Winston A. Douglas
*Assistant Examiner*—John F. Niebling
*Attorney, Agent, or Firm*—Murray Schaffer

[57] ABSTRACT

The invention relates to new esters of carboxylic acids formally substituted in the alpha-position by sodium or potassium which have the formula

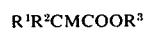

$$R^1R^2CMCOOR^3 \tag{1}$$

where
$R^1$ is H, $C_1$ to $C_{16}$ linear or branched alkyl, phenyl or tolyl
$R^2$ is $C_1$ to $C_6$ linear or branched alkyl,
$R^3$ is $C_1$ to $C_{12}$ linear or branched alkyl, and M is Na or K and to a method for their preparation consisting in the reaction of a carboxylic acid ester with An or K salt of hexamethyldisilazane. The reaction is carried out in a hydrocarbon medium which may contain up to 20 vol.-% of organic ether and at −80° to +50° C, while the molar ratio of amide salt to ester is 0.7 to 1.5. The preparation can be also carried out in the presence of alkali metal alkoxide $C_3$ to $C_{16}$ with the straight or branched molecule at the alkoxide - to - metallo ester ratios 0.5 to 20, giving the addition product of alpha-metallo ester and alkoxide. The invention further relates to the preparation of the aforesaid alpha-metallo esters by the exchange reaction between the ester of alpha.lithio carboxylic acid and Na or K alkoxide carried out at −40° to +50° C at the molar ratio of alkoxide to alpha-lithio ester 0.9 to 3.0 in a hydrocarbon medium. Instead of the pure alpha-lithio ester, also a fresh mixture prepared from alkyllithium compound, secondary amine and ester may be used. Alpha-sodio and alpha-potassio esters or their addition compounds with alkali metal alkoxides may be easily separated from the reaction mixture due to their insolubility either directly or after removing of solvents and volatile byproducts by distillation.

8 Claims, No Drawings

ESTERS OF CARBOXYLIC ACIDS FORMALLY SUBSTITUTED BY SODIUM OR POTASSIUM IN THE ALPHA-POSITION AND THE METHOD FOR THEIR PREPARATION

An objective of the invention are new esters or carboxylic acids formally substituted by sodium or potassium atoms in the alpha-position which have the general formula

   (1)

where
- $R^1$ is hydrogen atom, alkyl with 1 to 16 carbon atoms and the linear or branched chain, or phenyl or tolyl,
- $R^2$ is ALKYL with 1 to 6 carbon atoms in the straight or branched chain,
- $R^3$ is alkyl with 1 to 12 carbon atoms and the linear or branched chain,
- M is sodium or potassium atom.

Esters of carboxylic acids substituted in the alpha-position with alkali metals represent the reactive intermediates in numerous synthetic or polymerization reactions and therefore they have recently obtained considerable attention. Some of these compounds were prepared only in the reaction mixture till now, mostly by metallation reactions, and isolation of the pure form from the reaction mixture did not succeed. This method did not give satisfactory yields in the preparation of alpha-metallo ester based on the reaction of hexamethyldisilazyl sodium with carboxylic acid ester in tetrahydrofuran medium (M. W. Rathke: J. Am. Chem. Soc. 1970, 92, 3222) even at −78°C. The preparation of pure alpha-metallo esters was also unsuccessful in the diethyl ether medium as follows from the derivative analysis of reaction products (C. R. Kruger, E. G. Rochov; J. Organomet. Chem. 1964, 1, 476). These results are above all due to very fast condensation reactions of formed alpha-metallo esters in the organic ether medium which deteriorate the metallo esters. During the study of properties of alpha-metallo esters, the condensation reactions were found to proceed much slower in the hydrocarbon medium than in the ether solution (J. Baca, L. Lochmann, K. Juzl, J. Coupek, D. Lim: J. Polymer Sci., Part C, 1968, 16, 3865; L. Lochmann, D. Lim: J. Organomet. Chem. 1973, 50, 9; L. Lochmann, M. Rodova, J. Petranek, D. Lim: J. Polymer Sci., Chem. Edit., in press).

This is the reason why the experiments with preparation and isolation of pure alpha-metallo esters were carried out in the hydrocarbon medium. It has been found that the metallation reactions proceed with a sufficient rate also in this medium yielding alpha-metallo esters in absence of a substantial amount of the side condenation reactions. Pure alpha-lithio esters were prepared in this way (Czechoslovak Patent no. 153,790) and now we have succeeded also in obtaining the individual derivatives of the more heavy alkali metals by treatment of esters or carboxylic acids by salts of substituted organic amides. This preparation method is very simple and proceeds under convenient conditions giving alpha-metallo esters of relatively high purity.

It has been further found that the aforesaid alpha-metallo ester may be also prepared in a good yield by an exchange reaction according to the equation

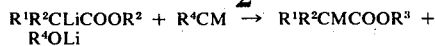

where M means Na or K; $R^1$ and $R^2$ is alkyl or aryl, and $R^3$ and $R^4$ is alkyl.

The above indicated position of metal bonding in alpha-metallo esters has to be understood formally, because also other isomeric structures of metallo esters can be theoretically derived, as e.g. a structure where the metal is bonded to the oxygen atom of the ester enol form. The definite structure of the alpha-metallo ester has not yet been ascertained, however the structure characterized by the metal bonded to carbon in the alpha-position to the carboxyl group is very probable and therefore it is used here.

The invention relates to new esters of carboxylic acids formally substituted in the alpha-position with sodium or potassium according to the above given formula I.

Another objective of the invention is the method for preparation of new esters of carboxylic acids formally substituted in the alpha-position with sodium or potassium by the reaction of esters of carboxylic acids with the sodium or potassium salt of hexamethyldisilazane, wherein the reaction is carried out in an inert solvent, preferably in aliphatic, cycloaliphatic, or aromatic hydrocarbons or their mixtures, if required also with addition of up to 20 volume percent of organic ether, at the temperature −80° to +50°C, preferably at the temperature +20°C.

Another objective of the invention is that the molar ratio of amide alkaline salts to ester during the reaction is 0.7 to 1.5.

Further objective of the invention is also that the reaction is carried out in the presence of alkali metal alkoxide which contains 3 to 16 carbon atoms in the straight or branched chain in the amount given by the alkali metal alkoxide - to -alpha-metallo ester ratio between 0.5 and 20.

Alpha-sodio or alpha-potassio ester formed is isolated according to the invention on the basis of its insolubility, possibly also after removing of the solvent and of volatile reaction products by distillation. Alpha-sodio and alpha-potassio esters of relatively high purity are isolated in this way.

An objective of the invention is also the further method for preparation of new esters of carboxylic acids formally substituted in the alpha-position with sodium or potassium having the general formula I which consists in treating the ester of analogous alpha-lithio carboxylic acid with sodium or potassium alkoxide containing 3 to 16 carbon atoms in the straight or branched chain at the alkoxide - to -alpha-lithio ester ratio ranging from 0.9 to 3.0 and the temperature −40° to +50°C, advantageously at 0°C, in the medium of aliphatic, cycloaliphatic or aromatic hydrocarbons or their mixture. Alpha-lithio ester is used in this process either as a pure isolated compound or as a freshly prepared reaction mixture from substituted lithium amide and ester or by mixing the organolithium compound, secondary amine and ester in a suitable solvent.

Finally, an objective of the invention is that the product of the exchange reaction, i.e., the obtained ester of carboxylic acid substituted with the more heavy alkali metal, is isolated from the reaction mixture on the basis of insolubility, possibly also after removing the solvent and volatile reaction products by distillation.

Utilizing of alpha-metallo ester in a form of the reaction mixture has numerous disadvantages. The reaction mixtures contain besides alpha-metallo esters also other compounds which may affect their reactions. It is also impossible to meter alpha-metallo esters into further reactions in an optimal ratio as determining of their actual concentration is very difficult and uneconomic. On the other hand, application of individual and pure alpha-metallo esters avoids the above shortcomings. In addition to it, the isolated alpha-metallo esters are substantially more stable than in ether solutions and can be stored for several months without change, which fact is convenient in their handling. Eventually, the method according to this invention is less expensive than other known preparations of metallo esters in the reaction mixture because it uses cheap hydrocarbons as the reaction medium and may be carried out at the ambient temperature instead of lower temperatures used until now.

It has been found formerly, that alkali metal alkoxides exhibit a favourable effect on the alpha-metallo esters reactivity. They enhance their stability towards condensation reactions (L. Lochmann, M. Rodova, J. Petranek, D. Lim: J. Polymer Sci., Chem. Edit., in press) and protect them from decomposition in this way. Moreover, alkali metal alkoxides increase also the efficiency of alpha-metallo esters in some reactions, for instance in the initiation of anionic polymerization of methacrylicmesters (L. Lochmann, J. Trekoval: U.S. Ser.No. 525,854 filed Nov. 12, 1974.

When the described metallation reaction of carboxylic acid esters is carried out in the presence of alkali metal alkoxide, an addition product of alpha-metallo ester with alkoxide is directly formed. Consequently, it is possible to prepare also these addition products in a simple and advantageous way according to this invention.

The invention is further illustrated in examples of performance without limiting its scope to the given facts. All operations with organic compounds of alkali metals were carried out in the nitrogen or argon atmosphere. Solvents were purified and then dried with lithium aluminium hydride. Reaction products were dried at the laboratory temperature in vacuum 1 mm Hg for at least 5 hours. The content of alkali metals was determined by the atomic absorption spectrometry.

EXAMPLE 1

Into the solution of 3.67 g of hexamethyldisilazyl sodium (0.020 mole) in 59 ml of benzene, 1.84 g of methyl isobutyrate (0.018 mole) was stepwise added at 20° C under stirring. The mixture was stirred for 2 hr and then allowed to stand at the ambient temperature for 15 hours. The separated precipitate was collected, washed with benzene and pentane. The yield was 2.23 g of methyl alpha-sodio isobutyrate, i.e. 100 % of theory. Na content found: 18.21 %, calculated: 18.56 %. IR spectrum corresponded to the proposed structure and confirmed the high purity of the product.

EXAMPLE 2

Into the solution of 2.34 g of hexamethyldisilazyl sodium (0.0129 mole) in 38 ml of benzene, 1.18 g of ethyl propionate (0.0116 mole) was stepwise added at 20° C under stirring. After 2 hr of stirring, the separated precipitate was collected and washed with benzene and pentane. The yield was 1.08 g of ethyl alpha-sodio propionate, i.e., 75.1 % of theory. Na content found: 18.15 %, calculated: 18.56 %. IR spectrum corresponded to the proposed structure and confirmed high purity of the product.

EXAMPLE 3

Into the solution of 2.34 g of hexamethyldisilazyl sodium (0.0169 mole) in 25 ml of toluene, 2.78 g of 2-ethylhexyl acetate (0.0161 mole) was stepwise added at 20° C under stirring. After 2 hr of stirring, the reaction product was isolated in the yield of 1.31 g of 2-ethylhexyl alpha-sodio acetate, i.e. 42.1 % of theory.

EXAMPLE 4

Into the solution of 3.10 g of hexamethyldisilazyl sodium (0.0191 mole) in 28 ml of toluene, 2.36 g. of ethyl isovalerate (0.0181 mole) was stepwise added at 20° C under stirring. The product was isolated after one hour of stirring in the yield of 2.28 g of ethyl alpha-sodio isovalerate, i.e. 84.1 % of theory.

EXAMPLE 5

Into the solution of 2.54 g of hexamethyldisilazyl sodium (0.0138 mole) in 13 ml of toluene, 4.33 g of ethyl stearate (0.0138 mole) in 13 ml of toluene was stepwise added at 20° C under stirring. The gel-like product was isolated after 1 hr by the gradual washing with heptane. The yield was 1.12 g of ethyl alpha-sodio stearate, i.e., 24.2 % of theory.

EXAMPLE 6

Into the solution of 3.42 g of hexamethyldisilazyl sodium (0.0186 mole) in 27.5 ml of toluene, 3.06 g of ethyl phenylacetate was added at 20° C under stirring. The separated voluminous precipitate was isolated after 1/2 hr of stirring in the yield of 2.92 g of ethyl alpha-sodio phenylacetate, i.e., 84.2 % of theory.

EXAMPLE 7

Into the solution of 3.54 g of hexamethyldisilazyl potassium (0.0177 mole) in 28 ml of toluene, 1.96 g of ethyl isobutyrate (0.0169 mole) was added at 20° C under stirring. After 2 hours of stirring, the separated precipitate was isolated in the yield of 1.91 g of ethyl alpha-potassio isobutyrate, i.e., 73.4% of theory.

EXAMPLE 8

Into a solution of 4.38 g of hexamethyldisilazyl sodium (0.0237 mole) and 2.28 g of sodium tert.butoxide (0.0237 mole) in 72 ml of toluene, 2.75 g of ethyl isobutyrate (0.0237 mole) was added at 20° C under stirring. After 2 hours, the resulting solution was concentrated to about 20 ml and the reaction product was isolated at the temperature −60° C. The yield was 1.83 g of addition compound of ethyl alpha-sodio isobutyrate with sodium tert.butoxide and the IR spectrum corresponded to the proposed structure.

EXAMPLE 9

A solution containing 0.0296 mole of ethyl alpha-lithio isobutyrate in 36 ml of cyclohexane was dropwise added under stirring into a solution of 0.0355 mole of sodium tert.butoxide in 35 ml of cyclohexane at 0° C within 3 minutes. The mixture was further stirred at the ambient temperature for 30 minutes and the separated precipitate was then isolated and fivetimes washed with cyclohexane. The yield was 84.4 % of the theoretical amount of ethyl alpha-sodio isobutyrate with the sodium content found 16.1 % (calculated 16.63 %). The product contained also 0.15 % of lithium. GLC analysis of the hydrolyzed sample gave the purity of ethyl alpha-sodio isobutyrate 93 %, while only traces of other compounds were visible in IR spectrum, in this case traces of ethyl sodio isobutyrylisobutyrate.

EXAMPLE 10

A solution of 0.0222 mole of ethyl alpha-lithio isobutyrate in 27 ml of cyclohexane was dropwise added under stirring into a solution containing 0.0266 mole of potassium (-)menthoxide in 25 ml of cyclohexane at the ambient temperature. After one hour, the mixture was worked out similarly as in Example 9 giving 43 % of the theoretical yield of ethyl alphapotassio isobutyrate with the potassium content 24.6 % (calculated 25.32 %). The content of lithium was 0.23 %. According to the GLC analysis of the hydrolyzed sample, the product contained 7 % of impurities (ethyl potassio isobutyrylisobutyrate). IR spectrum corresponded with other results of analysis.

EXAMPLE 11

A mixture prepared by subsequent mixing of 30 ml of heptane solution of n-butyllithium (c = 1.18 mole/l, i.e. 0.0355 mole), 0.0391 mole of diisopropylamine (dried over barium oxide), and 0.0302 mole of ethyl isobutyrate at −33° C was dropwise added to a suspension of 0.0355 mole of potassium tert.butoxide in 20 ml heptane at 0° C under stirring. The reaction mixture was stirred at the ambient temperature for 30 min, the separated precipitate was isolated and washed seventimes with heptane. The yield was 94.5 % of the theoretical amount of ethyl alpha-potassio isobutyrate, IR spectrum of which showed the similar purity as in Example 9. GLC analysis of the hydrolyzed sample gave the impurity concentration of 3.5 %; the content of nitrogen (Kjeldahl) was 0.23 % which is the evidence of the low extent of ester transamidation.

EXAMPLE 12

Into a suspension of 0.0272 mole of potassium tert.butoxide in 50 ml of benzene, 0.0266 mole of tert.butyl alpha-lithio isobutyrate was added and the mixture was shaken with three steel balls at the ambient temperature for 20 hr. The insoluble fraction was collected and washed seventimes with benzene giving tert.butyl alpha-potassio isobutyrate in the yield 68.3 % of theory. IR spectrum of the product exhibited the similar purity as at the product in Example 9.

We claim:
1. Esters of carboxylic acids substituted with sodium or potassium initially in the alpha-position of the general formula I

 (1)

where
R$^1$ is phenyl or tolyl,
R$^2$ is alkyl with 1 to 6 carbon atoms in the straight or branched chain
R$^3$ is alkyl with 1 to 12 carbon atoms in the straight or branched chain,
M is sodium or potassium.

2. Method for preparation of new esters of carboxylic acids substituted with sodium or potassium initially in the alpha-position of the general formula 1

 (1)

where R$^1$ is hydrogen, alkyl with 1 to 16 carbon atoms in the straight or branched chain, phenyl or tolyl,
R$^2$ is alkyl with 1 to 6 carbon atoms in the straight or branched chain
R$^3$ is alkyl with 1 to 12 carbon atoms in the straight or branched chain,
M is sodium or potassium by the reaction of esters of carboxylic acids with sodium or potassium salt of hexamethyldisilazane, wherein the reaction is carried out in an inert solvent, selected from the group consisting of in aliphatic, cycloaliphatic or aromatic hydrocarbons or their mixtures, with up to 20 volume percent of organic ether, at the temperataure −80 to +50°C.

3. Method for preparation as set forth in claim 2, wherein the molar ratio of sodium or potassium salt to ester is on the order of 0.7 to 1.5.

4. Method for preparation as set forth in claim 2, wherein the reaction is carried out in the presence of alkali metal alkoxide containing 3 to 16 carbon atoms in the straight or branched chain in the amount given by the alkali metal alkoxide - to - alpha-metallo ester ratio on the order of 0.5 to 20.

5. Method for preparation as set forth in claim 2, wherein isolation of the formed alpha-sodio or alpha-potassio ester of high purity from the reaction mixture is based on its insolubility which can be increased after removing the solvent and volatile reaction products by distillation.

6. Method for preparation of new esters of carboxylic acids according to claim 1, wherein ester of analogous alpha-lithio carboxylic acid is treated with sodium or potassium alkoxide containing 3 to 16 carbon atoms in the straight or branched chain at the temperataure −40° C to +50° C, in the medium of aliphatic, cycloaliphatic or aromatic hydrocarbons or their mixture, while the alkoxide - to - alpha-lithio ester molar ratio is on the order of 0.9 to 3.0.

7. Method for preparation as set forth in claim 6, wherein alpha-lithio ester is used either as the isolated pure compound or as the freshly prepared reaction mixture prepared from substituted lithium and ester or by mixing the organo-lithium compound, secondary amine and ester in a solvent selected from aliphatic, cycloaliphatic, and aromatic hydrocarbons and mixtures thereof.

8. Method for preparation as set forth in claim 6, wherein the product of the exchange reaction, i.e. the obtained ester of carboxylic acid substituted by the more heavy alkali metal, is isolated from the reaction mixture on the basis of its insolubility, which may be increased also after removing the solvent and volatile reaction products by distillation.

* * * * *